(12) United States Patent
Djurovic

(10) Patent No.: US 6,315,784 B1
(45) Date of Patent: Nov. 13, 2001

(54) SURGICAL SUTURING UNIT

(76) Inventor: Zarija Djurovic, 370 Devon Ct., Valparaiso, IN (US) 46383

(*) Notice: Subject to any disclaimer, the term of this patent is extended or adjusted under 35 U.S.C. 154(b) by 0 days.

(21) Appl. No.: 09/244,085

(22) Filed: Feb. 3, 1999

(51) Int. Cl.$^7$ ................................................. A61B 17/04
(52) U.S. Cl. .................................................. 606/146
(58) Field of Search .................... 606/222, 232, 606/144, 145, 148, 139, 146

(56) References Cited

U.S. PATENT DOCUMENTS

| | | | |
|---|---|---|---|
| 67,545 | * 8/1867 | Hodgins | 606/222 |
| 2,008,251 | * 7/1935 | Hillebrand | 606/146 |
| 2,737,954 | * 3/1956 | Knapp | 606/146 |
| 3,013,559 | * 12/1961 | Thomas | 606/146 |
| 3,638,653 | * 2/1972 | Berry | 606/146 |
| 4,011,873 | * 3/1977 | Hoffmeister | 606/146 |
| 5,207,693 | * 5/1993 | Phillips | 606/146 |
| 5,350,385 | * 9/1994 | Christy | 606/139 |
| 5,356,424 | * 10/1994 | Buzerak et al. | 606/223 |
| 5,431,666 | * 7/1995 | Sauer et al. | 606/139 |
| 5,437,266 | * 8/1995 | McPherson et al. | 606/217 |
| 5,653,716 | * 8/1997 | Malo et al. | 606/139 |
| 5,709,692 | * 1/1998 | Mollenauer et al. | 606/141 |
| 5,776,148 | * 7/1998 | Christy | 606/144 |

* cited by examiner

*Primary Examiner*—Henry J. Recla
*Assistant Examiner*—(Jackie) Tan-Uyen T. Ho

(57) ABSTRACT

A surgical suturing apparatus includes a needle, a needle holder which also serves as a support for suturing material, and an elongate handle. The needle defines a passageway through which the suturing material extends. The passageway has an outlet at the distal end of the needle.

9 Claims, 2 Drawing Sheets

SURGICAL SUTURING UNIT

BACKGROUND OF THE INVENTION

1. Field of the Invention

The present invention relates to a surgical device that will make it much easier for surgeons when performing surgeries to continuously or in an interrupted fashion suture different types of tissues. The present invention is capable of storing a large amount of suture material so suturing will be more or less without interruption, saving time in surgical procedures and cutting the cost of the surgical care.

2. Description of the Prior Art

In the present market there is no suitable suturing device that is capable of performing both suturing and the storing of suture material. The present invention is a needle and a spool, which can be made in different sizes. The invention is made to be relatively inexpensive, pre-sterilized, and disposable.

The prior art includes a variety of needle holders and free needles which are not suitable for use in many surgical procedures, but in the absence of anything better, surgeons are forced to use them, or to use other means of connecting different tissues, such as staplers or clips.

SUMMARY OF THE INVENTION

In accordance with one embodiment of the present invention, the surgical suturing apparatus includes a coil needle that can be made in different lengths, with ½ loops, one loop, or multiple loops. The coil needle is made of hypodermic tubing of different lumen gages to accommodate the passage of different types of suture material. The needle itself represents the distal end of the apparatus that finishes with a sharp tip and an opening that faces the outer radius of the coil.

The proximal end of the needle extends from the axial center of the coil and travels under an angle to fit in the channel define by the conic portion of the shaft where the tip of the conic portion will meet the beginning of the distal end of the needle in the needle's axial center.

The proximal end of the surgical suturing apparatus is a shaft which includes a conic portion in which the needle is secured, and a straight longitudinal portion on which the spool of suture material is placed.

There is a channel in the conic portion of the shaft that travels from the tip of the conus and finishes at the proximal end of the conic portion in such a way that it is under the same angle as the proximal end of the needle and the proximal opening is just above the edge of the distal portion of the spool.

The longitudinal portion of the shaft supports the spool and allows it to freely rotate. The very proximal end of the longitudinal portion is finished in a suitable way so that a surgeon may grasp it.

The spool is made to fit on the longitudinal portion of the shaft and has its own tubular cover to keep the suture material enclosed.

BRIEF DESCRIPTION OF THE DRAWINGS

For a more complex understanding of this invention, one should now refer to the embodiment illustrated in greater detail in the accompanying drawings and described below by way of an example of the invention. In the drawings.

While the following disclosure describes the invention in connection with one embodiment, one should understand that the invention is not limited to this embodiment and modification. Furthermore, one should understand that the drawings are not to scale and that graphic symbols, diagrammatic representatives, and fragmentary views, in part, illustrate the embodiment. In certain instances, the disclosure may not include details which are not necessary for an understanding of the present invention such as conventional details of fabrication and assembly.

DESCRIPTION OF THE PREFERRED EMBODIMENTS

For ease of reference, as used herein the term "distal" will refer to that part of the instrument which is farthest for the surgeon, and the term "proximal" refers to that part of the apparatus which is closest to the surgeon.

Figure 1:
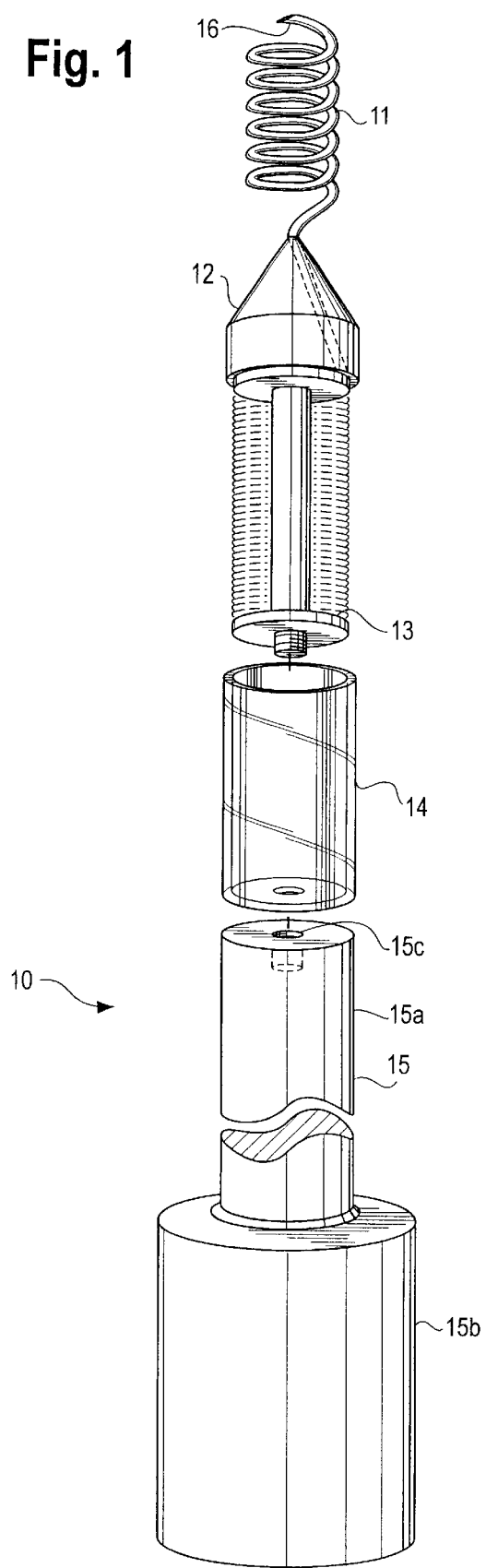
FIG. 1 is an exploded perspective view of a surgical suturing apparatus which includes a distal end and a proximal end.
Figure 2:
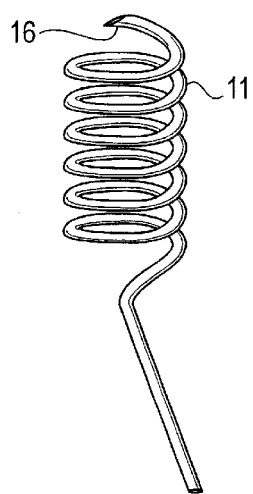
FIG. 2 is a perspective view of the coil needle showing the distal and proximal portions of the needle.

Turning now to the drawings and referring specifically to FIGS. 1 and 2, the surgical suturing apparatus of the present invention 10 generally includes a needle portion 11, a conic portion 12, a spool 13, a spool cover 14 and a handle 15. FIG. 2 shows the needle portion that includes a coil with a plurality of loops. Alternatively the needle portion may include only one loop or even one half of a loop.

The distal end of a needle portion 11 includes a tip 16 with an opening for the passage of suture material. The opening is made in such a way that it is on the top of the outside radius of the needle portion for a better presentation and easier grasping of the suture material.

The proximal end of stem of the needle portion is made under an angle and travels from the axial center of the coil, laterally toward the outside radius of the coil. The angle is equivalent to the angle of a channel 17 in the conic portion 12 in which the proximal end of the needle is secured.

Figure 3:
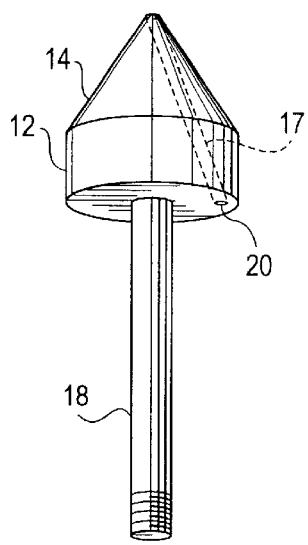
FIG. 3 is a perspective view of the conic portion.

FIG. 3 shows the conic portion 12 including a shaft 18 and a conic end 19 that defines the channel 17 and an opening 20.

The conic portion 12 is made in different outside diameter to be suitable for different passages. In the conic portion 12, the channel 17 travels from the tip, extending into the proximal horizontal portion of the conus under the angle that is the same as the angle of the proximal portion of the needle 11. The opening 20 of the channel 17 on the proximal horizontal surface of the conus is placed in the space between the circular portion of the distal end of the spool 13 and the spool cover 14 in such a way that it will allow free advancement of the suture material.

The shaft 18 of the conic portion 12 is placed in the central line of the handle 15 and serves as an axle for the spool 13 and the spool cover 14. The very end is threaded for attachment to the handle 15.

Figure 4:
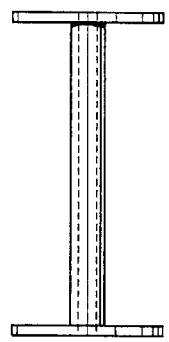
FIG. 4 is a side view of the spool used to hold the suture material in the present invention.

FIG. 4 shows the spool 13 which is made in such a way that the distal end is of smaller outside diameter than the inside diameter of the spool cover 14 to allow space for suture material to freely advance through the needle and also for the spool 13 to freely turn around the shaft 18. The proximal end of the spool is of the same outside diameter as the inside diameter of the spool cover with minimal tolerance to allow the spool to freely turn when covered. The length of the longitudinal portion 15 and the length of the spool 13 will depend on the type and amount of suture material needed (ie. the more suture material needed, the longer the spool and shaft).

Figure 5:
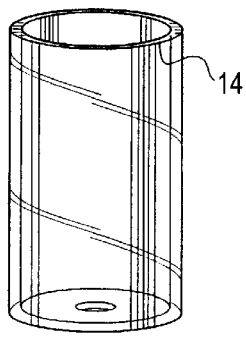
FIG. 5 is a perspective view of the Spool Cover.

FIG. 5 shows the spool cover 14 which is made to cover the spool 13 with suture material and to be of the same outside diameter as the conic portion 12. The distal end of the cover 14 is open and the proximal end has a central hole that is of the same diameter as the outside diameter of the handle 15 at the location.

Figure 6:
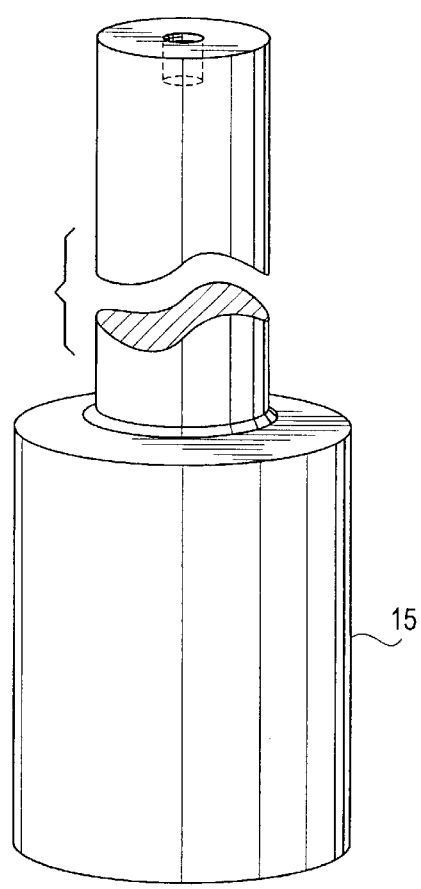
FIG. 6 is a perspective view of the longitudinal portion, including a shaft and a hand-piece.

FIG. 6 shows the handle 15 which includes a shaft portion 15a and hand-piece 15b. The shaft portion 15a is of the same outside diameter as the spool cover 14, and conic portion 12. On the tip of the shaft portion 15a there is a threaded bore 15c for the attachment of the conic portion 12. The hand-piece 15b is made to be suitable for an argonomic grasp by the surgeon's hand.

While the above description and the drawing disclose and illustrate one embodiment, one should understand, of course, that the invention is not limited to this embodiment. Those skilled in the art to which the invention pertains may make other embodiments employing the principles of this invention, particularly upon considering the foregoing teachings. Therefore, by the appended claims, the applicant intends to cover any modifications and other embodiments as incorporate those features which constitute the essential features of this invention.

What is claimed is:

1. A suturing apparatus comprising: a needle segment including a sharp distal end; a base segment having a first end portion holding the needle segment; a shaft segment having a first end connected to a second end portion of the base segment and extending axially therefrom; a spool of multiple winding of a continuous strand of suturing material rotatably mounted on the shaft segment; and a handle segment releasably secured to a second end of the shaft segment; the needle segment defining a passageway for directing suturing material to an outlet at the distal end of the needle segment; the second end of the shaft having a threaded end portion and the handle segment having a threaded bore that receives the threaded end portion of the shaft segment.

2. The suturing apparatus of claim 1, wherein the needle segment having a curved portion adjacent to the sharp distal end, the needle segment having a tube portion with a stem portion that extends into a corresponding bore in the first end portion of the base segment and with a coil portion including one or more spirals, the corresponding bore including an opening through which the suturing material extends to enter into the passageway of the needle segment.

3. The suturing apparatus of claim 1, wherein the distal end of the needle segment is angled from an outer radius to an inner radius of the coil and the outlet at the distal end of the needle facing outwardly of the coil.

4. The suturing apparatus of claim 1, wherein the base segment includes an enlarged portion and the shaft segment, the shaft segment serving as an axle for the spool around which the suturing material is wound.

5. The suturing apparatus of claim 4, wherein the enlarged portion is conical in shape and the needle and base segments form a straight, elongate structure.

6. The suturing apparatus of claim 4, further comprising a cover segment that extends over the spool of suturing material.

7. The suturing apparatus of claim 6, wherein the cover segment has a round tubular configuration.

8. The suturing apparatus of claim 1, wherein the needle segment, the base segment and the handle segment form a straight, elongate structure.

9. The suturing apparatus of claim 1, wherein the handle segment includes an elongate shaft portion and a hand-piece portion.

\* \* \* \* \*